(12) United States Patent
Lehnhardt et al.

(10) Patent No.: US 7,962,226 B2
(45) Date of Patent: Jun. 14, 2011

(54) COCHLEAR ENDOSTEAL ELECTRODE CARRIER MEMBER

(75) Inventors: Ernst Lehnhardt, Hannover (DE); Horst Hessel, Hannover (DE); Peter Gibson, South George (AU); John Parker, Roseville (AU); Ernst von Wallenberg, Basel (AU)

(73) Assignee: Cochlear Limited, Macquarie University, NSW (AU)

( * ) Notice: Subject to any disclaimer, the term of this patent is extended or adjusted under 35 U.S.C. 154(b) by 29 days.

(21) Appl. No.: 11/125,171

(22) Filed: May 10, 2005

(65) Prior Publication Data
US 2006/0079950 A1 Apr. 13, 2006

Related U.S. Application Data

(63) Continuation-in-part of application No. 10/473,925, filed as application No. PCT/AU02/00433 on Apr. 5, 2002, now abandoned.

(60) Provisional application No. 60/569,232, filed on May 10, 2004.

(30) Foreign Application Priority Data

Apr. 6, 2001 (AU) .................................... PR 4259
Feb. 21, 2002 (AU) .................................... PS 0686

(51) Int. Cl.
*A61N 1/05* (2006.01)

(52) U.S. Cl. ............ 607/136; 607/55; 607/56; 607/57; 607/137; 607/118; 607/152; 600/373

(58) Field of Classification Search .................. 607/137, 607/36, 55–7, 63, 115, 116, 118, 152, 136; 600/373
See application file for complete search history.

(56) References Cited

U.S. PATENT DOCUMENTS
4,261,372 A 4/1981 Hansen et al.
(Continued)

FOREIGN PATENT DOCUMENTS
AU 2002244531 A1 7/2006
(Continued)

OTHER PUBLICATIONS

J. Ito, et al, Tinnitus Suppression by Electrical Stimulation of the Cochlear Wall and by Cochlear Implantation: Department of Otolaryngology, Otsu Red Cross Hospital, Japan, The Laryngoscope vol. 104 (6 Pt. 1), Jun. 1994, pp. 752-754.

(Continued)

*Primary Examiner* — Carl H Layno
*Assistant Examiner* — Natasha N Patel
(74) *Attorney, Agent, or Firm* — Kilpatrick Townsend & Stockton LLP

(57) ABSTRACT

An elongate electrode carrier member including a longitudinally-extending central region, two side regions laterally extending from opposing sides of the central region, a lateral surface defined by the central and side regions together forming a convex circumferential surface, a medial surface defined by a convex surface of the central region and a concave surface for each of the side regions, a plurality of longitudinally-spaced electrodes disposed on or in the convex surface of the central region of the medial surface, and a support structure including a plurality of longitudinally extending wires each connected to one or more of the electrodes, wherein a subset of the plurality of wires is disposed in the central region and at least one of the plurality of wires is disposed in one of the side regions.

23 Claims, 9 Drawing Sheets

U.S. PATENT DOCUMENTS

| | | | |
|---|---|---|---|
| 4,532,930 | A | 8/1985 | Crosby et al. |
| 5,167,236 | A | 12/1992 | Junker |
| 5,443,493 | A * | 8/1995 | Byers et al. .................. 607/137 |
| 5,645,585 | A | 7/1997 | Kuzma |
| 5,795,287 | A | 8/1998 | Ball et al. |
| 5,814,095 | A | 9/1998 | Muller et al. |
| 6,070,105 | A | 5/2000 | Kuzma |
| 6,112,124 | A | 8/2000 | Loeb |
| 6,129,753 | A | 10/2000 | Kuzma |
| 6,198,971 | B1 | 3/2001 | Leysieffer |
| 6,259,951 | B1 | 7/2001 | Kuzma et al. |
| 6,537,200 | B2 | 3/2003 | Leysieffer et al. |
| 6,549,814 | B1 * | 4/2003 | Strutz et al. .................. 607/137 |
| 6,565,503 | B2 | 5/2003 | Leysieffer et al. |
| 6,575,894 | B2 | 6/2003 | Leysieffer |
| 6,697,674 | B2 | 6/2003 | Leysieffer et al. |
| 7,194,314 | B1 * | 3/2007 | Richter et al. ................. 607/57 |
| 7,315,763 | B2 | 1/2008 | Kuzma |
| 2004/0172118 | A1 | 9/2004 | Gibson |
| 2004/0236390 | A1 | 11/2004 | Dadd et al. |
| 2004/0243212 | A1 | 12/2004 | Dadd et al. |
| 2005/0080473 | A1 | 4/2005 | Gibson et al. |
| 2007/0135884 | A1 | 6/2007 | Risi |
| 2007/0135885 | A1 | 6/2007 | Risi |
| 2007/0167098 | A1 | 7/2007 | Beiter et al. |
| 2007/0282416 | A1 | 12/2007 | Gibson et al. |

FOREIGN PATENT DOCUMENTS

| | | |
|---|---|---|
| WO | WO 90/07251 | 6/1990 |
| WO | WO-9631087 | 10/1996 |
| WO | WO-9726943 | 7/1997 |
| WO | WO 00/69512 | 11/2000 |
| WO | WO 02/080817 | 10/2002 |
| WO | WO-2007027879 | 3/2007 |

OTHER PUBLICATIONS

M. Sakajri, et al.; "A method for Suppressing Tinnitus by Electrical Stimulation to Cochlea and Remedial Value"; Research Institute for Electric Science, Hokkaido University, Sapporo Japan, Journal of the Acoustical Society of Japan (E), vol. 14, No. 6, pp. 453-455, Nov. 1993.

W. McKerrow, et al., "Tinnitus Suppression by Cochlear Implants"; Coleman and Epstein Laboratories Department of Otolaryngology, University of California, San Francisco, The Annals of Otology, Rhinology & Laryngology, Jul. 1991, vol. 100 (7) pp. 552-558.

International Search Report for PCT/AU02/00433, dated May 28, 2002.

AU Examiner's Report dated Apr. 15, 2008.

JP Notice of Reasons for Rejection dated Aug. 5, 2008.

International Preliminary Examination Report for PCT/AU02/00433 dated Sep. 5, 2002.

International Preliminary Examination Report for PCT/AU02/00433 dated Sep. 5, 2002.

English Translation of Japanese Notice of Reasons for Rejection, mailed Jan. 15, 2008, in connection with Patent Application No. 2002-578856 (3 Pages).

* cited by examiner

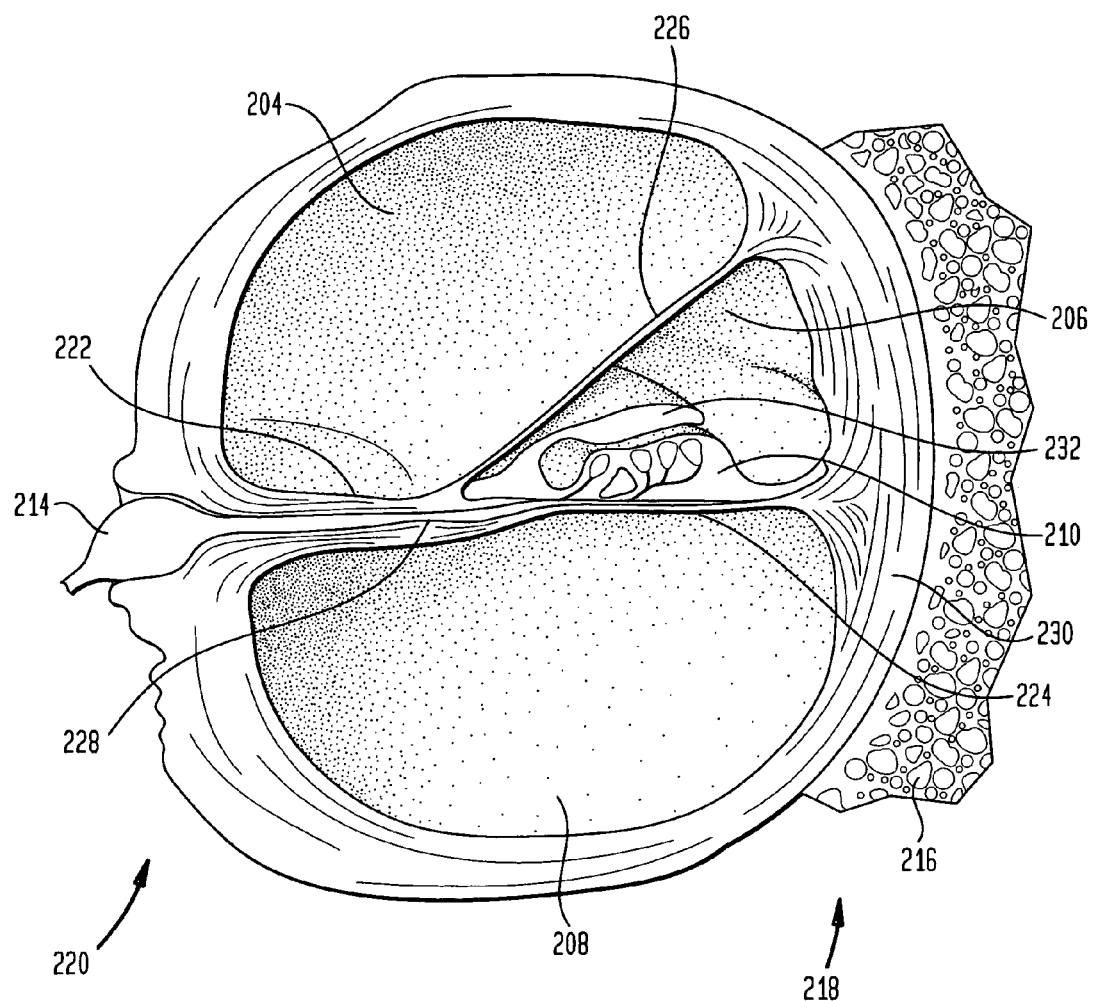

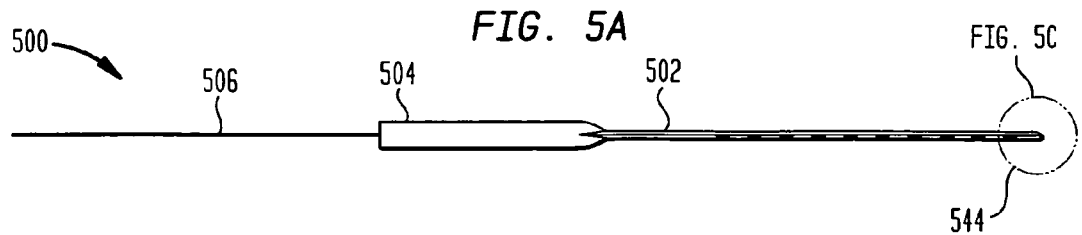
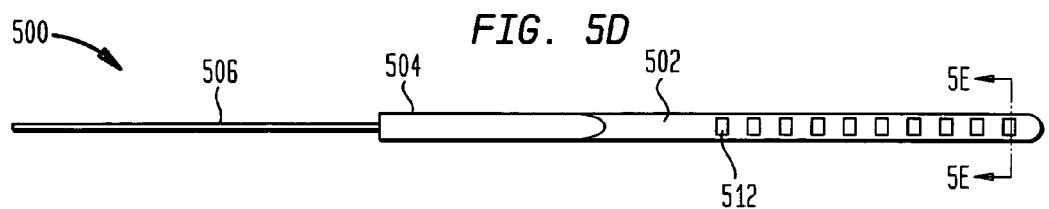
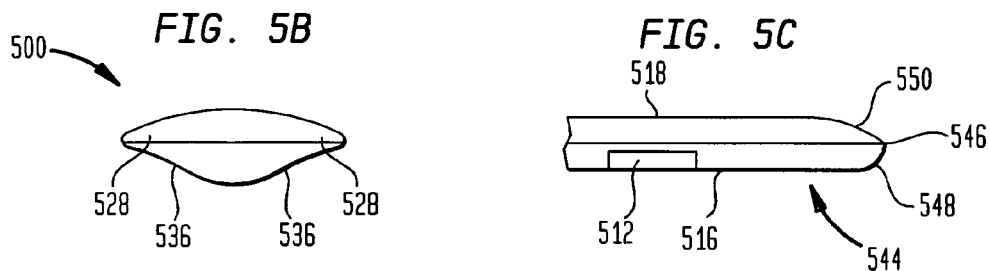
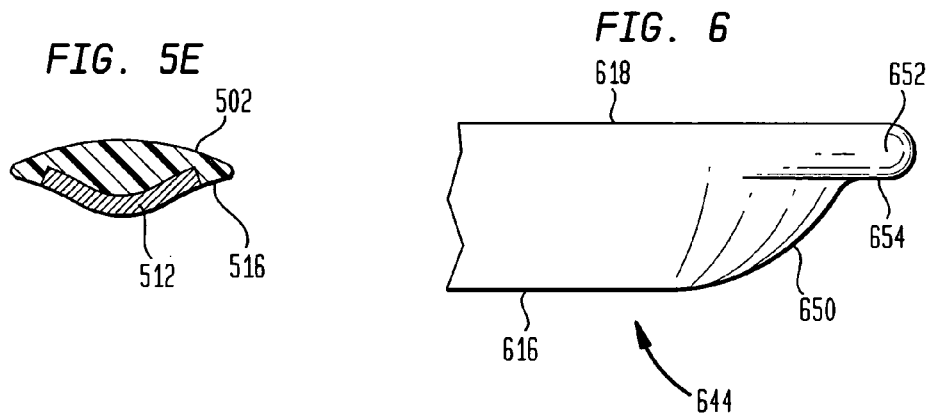

COCHLEAR ENDOSTEAL ELECTRODE CARRIER MEMBER

CROSS-REFERENCE TO RELATED APPLICATIONS

This application is a continuation-in-part of U.S. application Ser. No. 10/473,925, entitled "Endosteal Electrode" filed Dec. 10, 2004, which is a national stage patent application of international application number PCT/AU02/00433, entitled "Endosteal Electrode" filed Apr. 5, 2002, which claims priority of Australian Application No. PR 4259, entitled "Endosteal Electrode" filed Apr. 6, 2001, and Australian Application No. PS 0686 entitled "Tinnitus Treatment System" filed Feb. 21, 2002. This application also claims the priority of U.S. Provisional Patent Application 60/569,232 entitled "Biomechanical and Functional Optimized Endosteal Electrode," filed May 10, 2004. The above applications are hereby incorporated by reference herein in their entirety.

BACKGROUND

1. Field of the Invention

The present invention relates generally to an auditory prosthesis and, more particularly, to an endosteal electrode carrier member for use with an auditory prosthesis to stimulate the cochlea.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids, which amplify sound so that acoustic information can reach the cochlea.

In many people who are profoundly deaf, however, the reason for their deafness is sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to or absence of the mechanism for naturally generating nerve impulses from sound.

It is for this purpose that another type of auditory prosthesis, a cochlear implant (also commonly referred to as cochlear prostheses, cochlear devices, cochlear implant devices, and the like; generally and collectively referred to has "cochlear implants" herein) has been developed. These types of auditory prostheses bypass the hair cells in the cochlea, directly delivering electrical stimulation to the auditory nerve fibers via an implanted electrode assembly. This enables the brain to perceive a hearing sensation resembling the natural hearing sensation normally delivered to the auditory nerve.

Despite the enormous benefits offered by cochlear implants, one potential disadvantage of placement of the electrode assembly within the scala tympani is that it is necessary to breach the internal canals of the cochlea, generally the scala tympani. Breaching the scala tympani may adversely affect the hydrodynamic behavior of the cochlea and/or damage existing hair cells thereby preventing or at least reducing the likelihood that any residual hearing of the recipient will be preserved. This may be problematic for those persons who would benefit from use of an implantable hearing device to improve hearing of relatively high frequencies but who have some residual hearing of relatively low frequencies. In such a case, the recipient is forced to trade off an existing residual capacity to hear relatively low frequency sounds against the desirability of being able to have a hearing sensation of relatively high frequency sounds offered by an implantable hearing device.

SUMMARY

In one aspect of the invention, an elongate carrier member is disclosed. The carrier member comprises: longitudinally-extending central and side regions, the side regions laterally extending from opposing sides of the central region such that the carrier member is substantially symmetrical about a longitudinal plane, the central and side regions together forming a convex circumferential surface defined by a single radius and a medial surface defined by a convex surface of the central region and a concave surface of the side regions, wherein transitional surfaces between the medial and circumferential surfaces have a minimum radius greater than zero; and a plurality of longitudinally-spaced electrodes disposed at the convex surface of the central region.

BRIEF DESCRIPTION OF THE DRAWINGS

FIG. 2B is a cross-sectional view of one turn of the canals of the cochlea illustrated in FIG. 2A.

FIG. 5A is a side view of an electrode system having an endosteal electrode carrier member in accordance with an alternative embodiment of the present invention.

FIG. 5B is a front view of the endosteal electrode carrier member illustrated in FIG. 5A, in accordance with one embodiment of the present invention.

FIG. 5C is an enlarged side view of the tip region of the endosteal electrode carrier member illustrated in FIG. 5A.

FIG. 5D is a top view of the endosteal electrode carrier member illustrated in FIG. 5A, in accordance with one embodiment of the present invention.

FIG. 5E is a cross sectional view of the endosteal electrode carrier member illustrated in FIG. 5D, in accordance with one embodiment of the present invention.

FIG. 6 is an enlarged side view of the tip region of an endosteal electrode carrier member of the present invention, in accordance with one embodiment of the present invention.

DETAILED DESCRIPTION

The present invention is generally directed to an elongate electrode carrier member for implantation in a location external to the cochlear canals to position at least one, and likely many, electrodes sufficiently proximate to the organ of Corti to effectively deliver stimulation signals to the auditory nerve fibers of the cochlea. Generally, the carrier member is dimensioned to be implanted in a crevice, channel or pocket formed between the spiral ligament and bony capsule of the cochlea. Embodiments of the carrier member preferably have a minimized volume to accommodate insertion into such a crevice. In addition, embodiments of the carrier member comprise an elongate bulbous central region having electrodes disposed on the medial surface thereof, and elongate tapered side regions laterally extending from the central region. The side regions have rounded edges and are preferably flexible, while the carrier is configured to coil or turn toward the medial surface. This construction facilitates implantation of the carrier member: the carrier member has sufficient longitudinal strength to maintain its form and direction while being pushed into the surgically-formed crevice, and coils in a longitudinal plane to follow the contour of the cochlea, while the side regions serve to guide the direction of travel, flexing out of the lateral plane as necessary to avoid damaging anatomical structures. Once implanted, embodiments of the carrier member are urged to remain in its implanted position due to one or more of either the side regions extending into the corners of the crevice, and/or due to the curved lateral surface of the carrier member which approximates the curvature of the endosteum along the basal turn of the cochlea.

The present invention offers numerous advantages not provided by conventional systems and approaches. For example, one advantage is that such an implant provides an alternative option for those persons who would benefit from the use of an implantable hearing device to improve hearing of relatively high frequencies but who have some residual hearing of relatively low frequencies. Another advantage is that embodiments of the present invention provide an electrode array to be positioned to stimulate desired neurons without risking infiltrating the canals of the cochlea, thereby preserving the normal hydrodynamic nature of the cochlea.

Furthermore, advantages can be realized in applications other than creation of a hearing sensation. For example, embodiments of the present invention may also be used as a means of masking the symptoms of tinnitus. In such applications, embodiments of the present invention may treat the symptoms of tinnitus, while not requiring complicated surgery nor the fixation of electromechanical transducers to the ossicles.

Figure 1A:
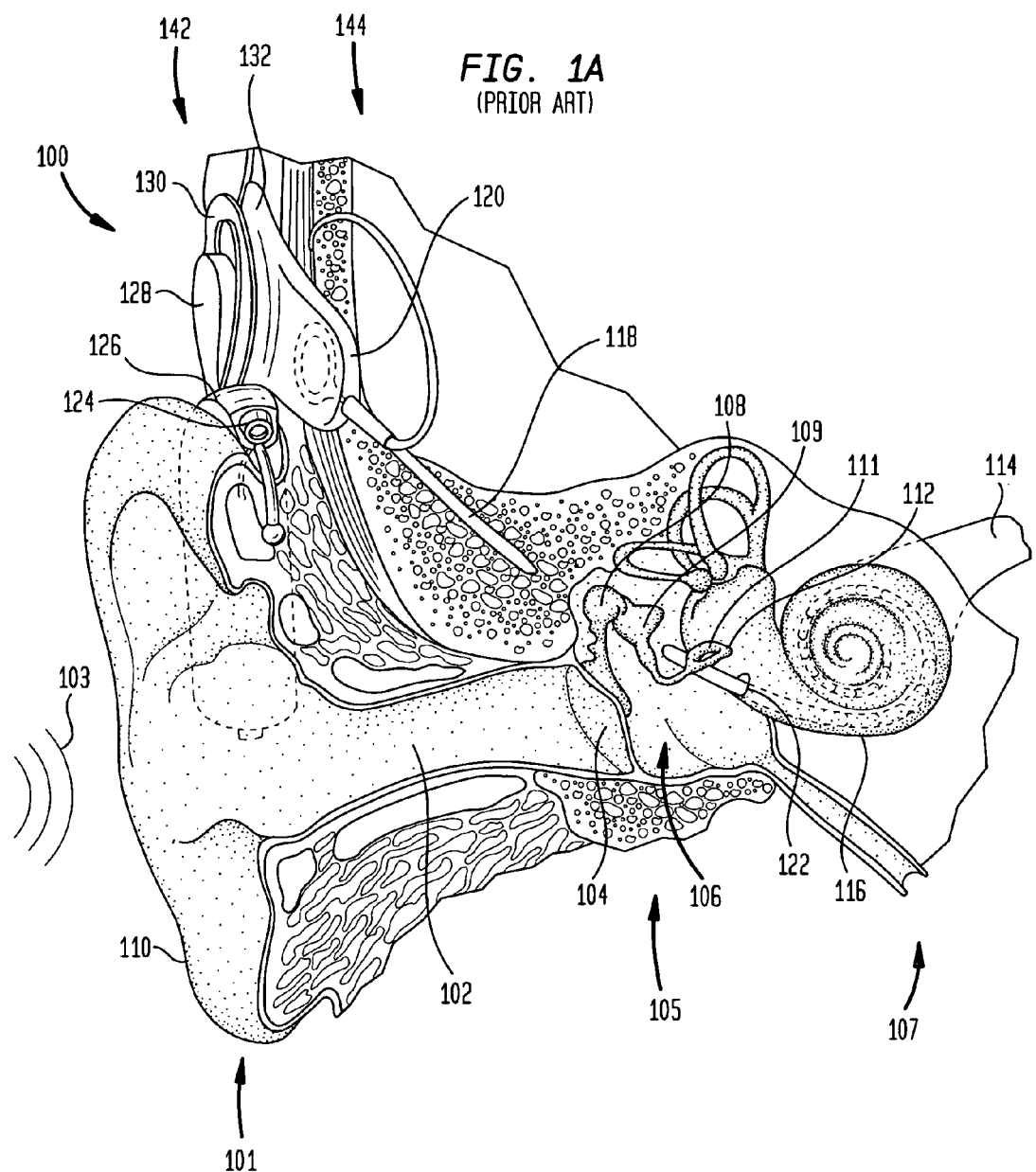
FIG. 1A is a pictorial representation of a conventional cochlear implant.
Figure 1B:
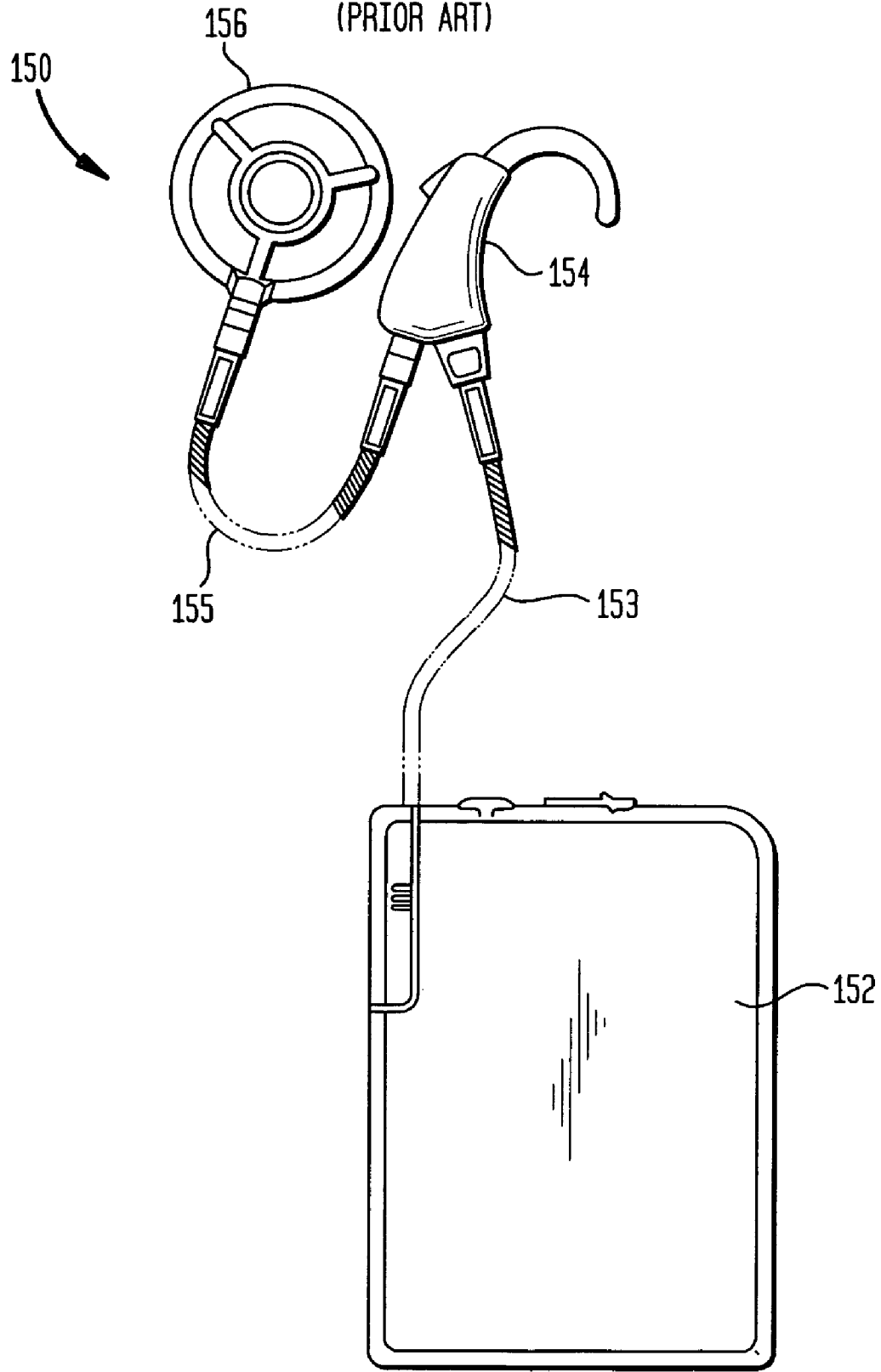
FIG. 1B is a perspective view of an alternative embodiment of the external component which may be utilized in the exemplary cochlear implant illustrated in FIG. 1A.

FIG. 1A is a pictorial representation of a conventional cochlear implant device implanted in a human cochlea. FIG. 1B is a perspective view of an alternative embodiment of the external component which may be utilized in the exemplary cochlear implant illustrated in FIG. 1A.

Referring now to FIG. 1, the relevant components of outer ear 101, middle ear 105 and inner ear 107 are described next below. In a fully functional ear outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to acoustic wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify the acoustic wave 103, causing oval window 112 to articulate, or vibrate. Such vibration sets up waves of fluid motion within cochlea 140. Such fluid motion, in turn, activates tiny hair cells (not shown) that line the inside of cochlea 140. Activation of the hair cells causes appropriate nerve impulses to be transferred through the spiral ganglion cells and auditory nerve 114 to the brain (not shown), where they are perceived as sound.

Conventional cochlear implant system 100 comprises external component assembly 142 which is directly or indirectly attached to the body of the recipient, and an internal component assembly 144 which is temporarily or permanently implanted in the recipient. External assembly 142 typically comprises microphone 124 for detecting sound, a speech processing unit 126, a power source (not shown), and an external transmitter unit 128. External transmitter unit 128 comprises an external coil 130 and, preferably, a magnet (not shown) secured directly or indirectly to external coil 130. Speech processing unit 126 processes the output of audio pickup devices 124 that are positioned, in the depicted embodiment, by ear 110 of the recipient. Speech processing unit 126 generates coded signals, referred to herein as a stimulation data signals, which are provided to external transmitter unit 128 via a cable (not shown).

Internal components 144 comprise an internal receiver unit 132, a stimulator unit 120, and an electrode assembly 118. Internal receiver unit 132 comprises an internal transcutaneous transfer coil (not shown), and preferably, a magnet (also not shown) fixed relative to the internal coil. Internal receiver unit 132 and stimulator unit 120 are hermetically sealed within a biocompatible housing. The internal coil receives power and data from external coil 130, as noted above. A cable or lead of electrode assembly 118 extends from stimulator unit 120 to cochlea 140 and terminates in an electrode array. Signals generated by stimulator unit 120 are applied by the electrodes to cochlea 140, thereby stimulating the auditory nerve 114.

In one embodiment, external coil 130 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, implantable receiver unit 112 may be positioned in a recess of the temporal bone adjacent ear 122 of the recipient.

External assembly 142 of cochlear implant 100 may have different configurations and arrangements. FIG. 1B is a perspective view of one embodiment of external assembly 142, referred to as external assembly arrangement 150. In arrangement 150, a body-worn speech processing unit 152 is connected to a headset unit 154 with a first cable 153. Headset unit 154 is, in turn, connected to a transmitter coil 156 with a second cable 155.

In this exemplary embodiment, headset unit 154 comprises three audio pickup devices (not shown). In one embodiment, the audio pickup devices are microphones, although in alternative embodiments the audio pickup devices can be telecoils or other similar devices now or later developed. Each audio pickup device detects and converts ambient sound into an electrical audio signal. The electrical audio signals are transmitted over cable 153 to speech processing unit 152, which contains appropriate speech processing circuitry to convert the electrical audio signals into electrical coded stimulation signals according to a particular speech processing strategy. The stimulation signals are transmitted via cable 153 from speech processing unit 152 to headset unit 154, and from headset unit 154 to external coil 156 via cable 155, for transmission over an RF link to implanted stimulator unit 120 (FIG. 1A).

Further details of a conventional cochlear implant device may be found in U.S. Pat. Nos. 4,532,930, 6,537,200, 6,565,503, 6,575,894 and 6,697,674, which are hereby incorporated by reference herein in their entirety.

Figure 2A:
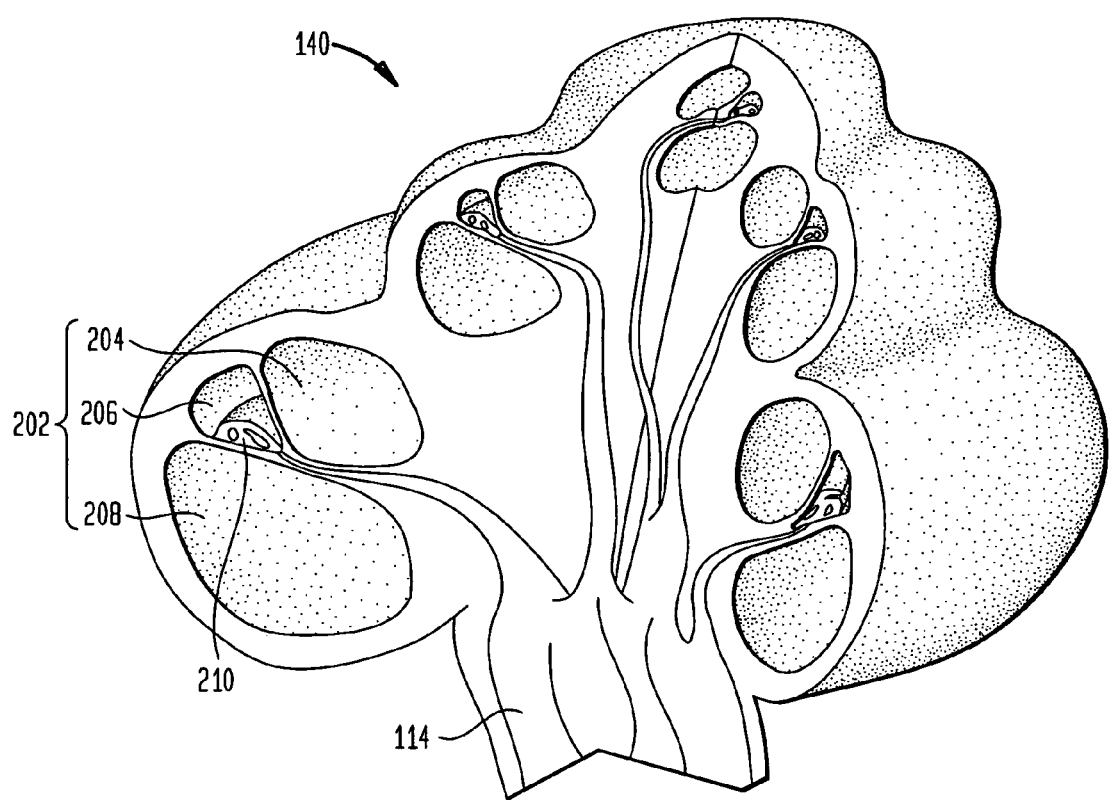
FIG. 2A is a perspective view of a cochlear partially cut-away to display the canals and verve fibers of the cochlea.

The human cochlea is described next below with reference to FIGS. 2A and 2B. FIG. 2A is a perspective view of a human cochlea partially cut-away to display the canals and nerve fibers of the cochlea. FIG. 2B is a cross-sectional view of one turn of the canals of the cochlea illustrated in FIG. 2A. To facilitate understanding, the following description will reference to the cochlea introduced above with reference to FIG. 1A, cochlea 140. It should be appreciated that embodiments of the present invention may be implanted in any cochlea to provide therapeutic benefits for a variety ailments now or later discovered.

Referring to FIG. 2A, cochlea 140 is a conical spiral structure comprising three parallel fluid-filled canals, one or more of which are sometimes referred to as ducts. The canals, collectively and generally referred to herein as canals 202, comprise the tympanic canal 208, also know as the scala tympani, the vestibular canal 204, also referred to as the scala vestibuli, and the median canal 206, also referred to as the cochlear duct. Tympanic and vestibular canals 208, 204 transmit pressure, while medial canal 206 contains the organ of Corti 210 which detects pressure impulses and responds with electrical impulses which travel along the auditory nerve fibers 114 to the brain (not shown).

Referring now to FIG. 2B, separating the three canals 202 of cochlea 140 are various membranes and other tissue. The Ossicous spiral lamina 222 separates scala vestibuli 204 from the scala tympani 208. Toward lateral side 218 of scala tympani 208, the basilar membrane 224 separates scala tympani 208 from cochlear duct 206. Similarly, toward lateral side 218 of scala vestibuli 204, the vestibular membrane 226, also referred to as the Reissner's membrane 226, separates scala vestibuli 204 from cochlear duct 206.

The fluid in tympanic and vestibular canals 208, 204, referred to as perilymph, has different properties than that of the fluid endolymph which fills cochlear duct 206 and surrounds organ of Corti 210. Sound entering the ear 110 causes pressure changes in cochlea 140 to travel through the fluid-filled tympanic and vestibular canals 208, 204. As noted, organ of Corti 210 is situated on basilar membrane 224 in cochlear duct 206. It contains rows of 16,000-20,000 hair cells (not shown) which protrude from its surface. Above them is the tectoral membrane 232 which moves in response to pressure variations in the fluid-filled tympanic and vestibular canals 208, 204. Small relative movements of the layers of membrane 232 are sufficient to cause the hair cells to send a voltage pulse or action potential down the associated nerve fiber 228. Nerve fibers 228, embedded within spiral lamina 222, connect the hair cells with the spiral ganglion cells 214 which form auditory nerve fibers 114. These impulses travel to the auditory areas of the brain for processing.

The place along the basilar membrane where maximum excitation of the hair cells occurs determines the perception of pitch and loudness according to the place theory. Due to this anatomical arrangement, the cochlea has characteristically been referred to as being "tonotopically mapped." This property of cochlea 140 has traditionally been exploited by providing implantable elongate members 120 having electrodes 122 each constructed and arranged to deliver to a selected region within scala tympani 208 a stimulating signal within a predetermined frequency range.

Portions of cochlea 140 are encased in a bony capsule 216. Referring to FIG. 2B, cochlear bony capsule 216 resides on the lateral side 218 (the right side as drawn in FIG. 2B), of cochlea 140. Spiral ganglion cells 214 reside on the opposing medial side 220 (the left side as drawn in FIG. 2B) of cochlea 140. A spiral ligament membrane 230 is located between lateral side 218 of spiral tympani 208 and bony capsule 216, and between lateral side 218 of cochlear duct 206 and bony capsule 216. Spiral ligament 230 also typically extends around at least a portion of lateral side 218 of scala vestibuli 204.

In accordance with the teachings of the present invention, embodiments of the electrode carrier member are configured to be implanted in a crevice formed between spiral ligament 230 and the endosteum (not shown) of cochlea bone 216. FIG. 3B is a perspective view of an exemplary hearing prosthesis 300 utilizing an endosteal carrier member according to one embodiment of the present invention. Such a device is referred to herein as a hybrid cochlear implant since it provides direct electrical stimulation of nerve cells 228 located in cochlea 140, thereby enhancing the hearing of selected frequencies, while simultaneously relying on the recipient's normal hearing processes, e.g., the recipient's residual hearing.

As will become apparent from the present disclosure, embodiments of the carrier member of the present invention may be used to provide therapeutic benefits in a variety of applications. In one exemplary application, embodiments of the present invention are configured to be utilized to improve the hearing of relatively high frequencies in those recipients who have residual hearing of relatively low frequencies. The spiral ganglion and other cells responsible for the perception of high frequency sounds are generally located at basal end 116 of cochlea 140. For those individuals who suffer from high frequency hearing loss, the hair cells in basal region 116 of cochlea 140 are ineffective or otherwise damaged. In such application, exemplary hearing prosthesis 300 utilizing an endosteal carrier member according to one embodiment of the present invention provides direct electrical stimulation of basal nerve cells 228 located in cochlea 140, thereby enhancing the hearing of high frequency sounds, while simultaneously relying on the recipient's normal hearing processes; that is, the recipient's residual low and mid frequency hearing, to sense low-to-mid frequency sounds.

Figure 3A:
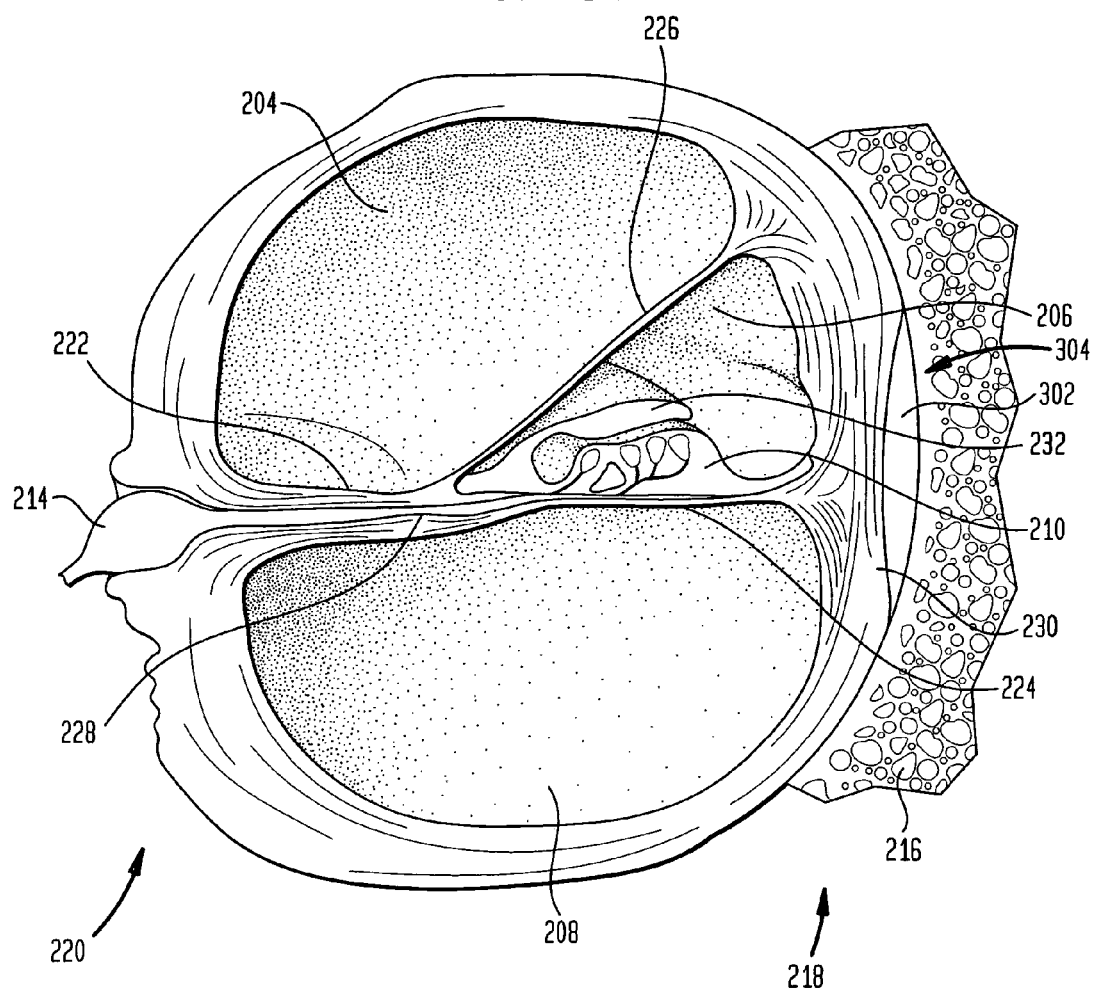
FIG. 3A is a cross-sectional view of the cochlea illustrated in FIG. 2B after a pocket is surgically formed between the cochlea and its supporting bone structure, in accordance with one embodiment of the present invention.
Figure 3B:
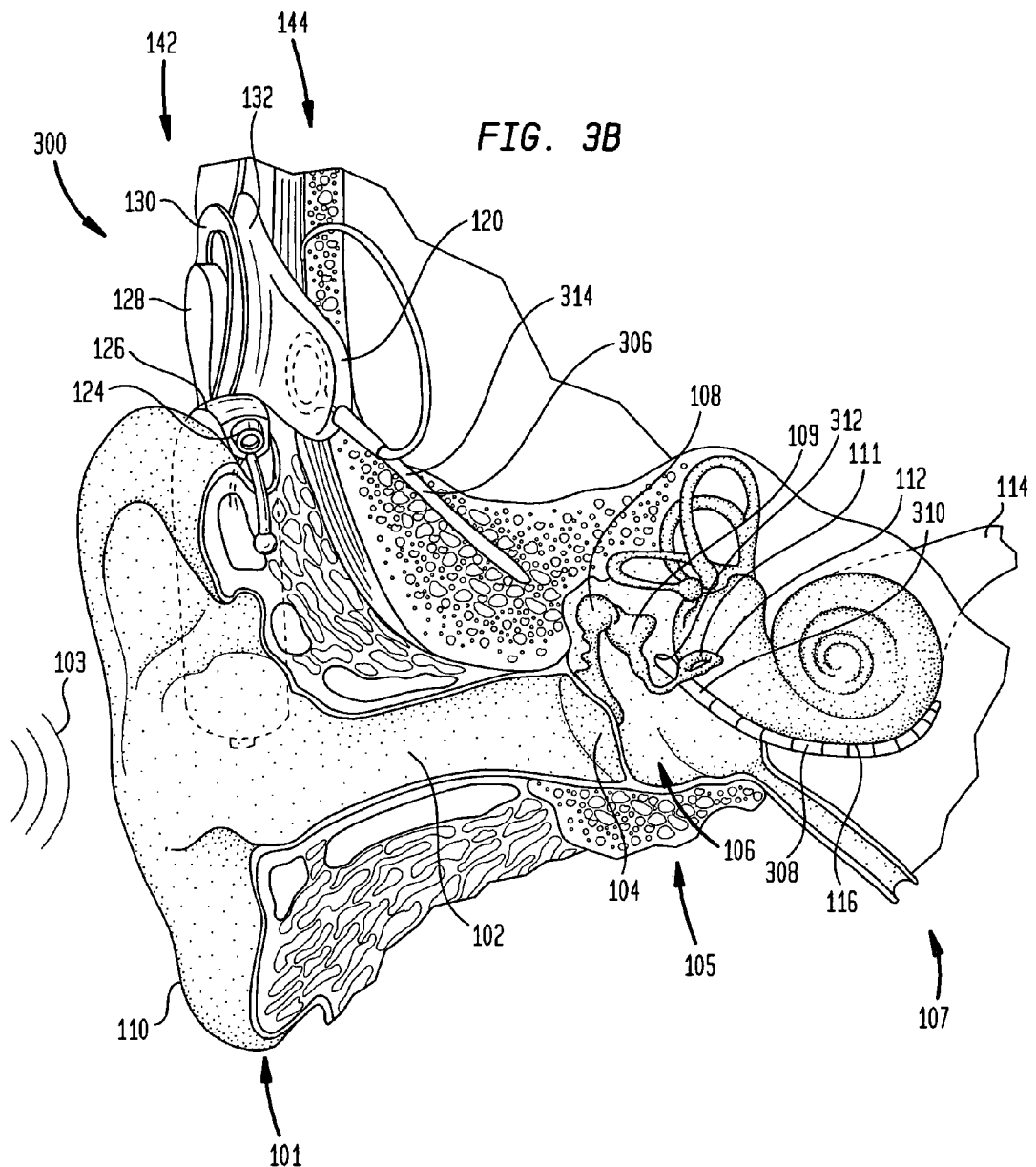
FIG. 3B is a perspective view of an exemplary hearing prosthesis utilizing an endosteal carrier member according to one embodiment of the present invention.

FIG. 3A is the same cross-sectional view illustrated in FIG. 2B, illustrating an exemplary crevice 302 surgically formed between spiral ligament 230 and the endosteum of cochlea bone 216. Crevice 302 may be surgically formed, for example, by separating spiral ligament 230 from cochlear bony capsule 216. Such surgical techniques are considered to be well-known to those of ordinary skill in the art and, therefore, are not described further herein. In the embodiment shown in FIG. 3A, crevice 302 is formed at the basal turn 304 of cochlea 140. It should be appreciated, however, that in alternative embodiments, a crevice similar to crevice 302 may be formed in other locations in cochlea 140 exterior to canals 202.

The placement of a device according to embodiments of the present invention is preferably designed to avoid any breach of the internal canals 202 of cochlea 140; that is, scala tympani 208, scala vestibule 204 and cochlear duct 206. This insures the normal hydrodynamic behavior of the cochlea is not affected by the implantation of a carrier member of the present invention. This may be advantageous, for example, for recipients suffering tinnitus and other ailments in which there may be significant functional hearing which may be preserved. For recipients with at least some sensorineural hearing loss, use of the device maximizes the possibility of also preserving residual hearing offered by the recipient's cochlea. In this case, it is envisaged that use of the device will have particular benefit in those instances where the recipient has substantial residual hearing in the low frequencies but would benefit from supplemental stimulation in a relatively higher frequency range. In this case, the recipient may benefit from use of a hearing aid that amplifies the relatively low frequencies still detectable by the recipient and an implantable hearing device for detection of relatively high frequencies.

A cochlear implant system 300 incorporating a carrier member of the present invention will now be described with reference to FIG. 3B. System 300 comprises implantable stimulator/receiver unit 120 implanted near ear 110, and a cochlear electrode assembly 306 having a plurality of spaced apart electrodes 308 disposed on a carrier member 310 of the present invention. Carrier member 310 is inserted into cochlea 140 through a soft cochleostomy 312, adjacent oval window 112. A lead 314 electrically connects the electrodes 308 on carrier member 310 to stimulator unit 120. As one of ordinary skill in the art would appreciate, although lead 314 is depicted passing through middle ear 105 in FIG. 3B, in practice lead 314 is typically tunneled through tissue that bypasses or goes around middle ear 105 so as not to interfere with the operation of the ossicles 106 within middle ear 105.

Stimulator unit 120 is coupled to an external microphone 124 that detects sound. Microphone 124 generates signals which are amplified and processed by a suitable speech processor 126. As noted, speech processor 126 may be external or implanted. Speech processor 126 generates appropriate control signals that are coupled to stimulator unit 120. Such coupling may occur through various means, as is well-known in the art, but is usually achieved through an inductive coupling link as described above with reference to FIG. 1A. It should be understood that in alternative embodiments speech processor 126 and power source (not shown) are implanted, either as an integral part of stimulator unit 120, or in a separate housing coupled to stimulator unit 120.

In operation, speech processor 126 performs signal processing operations to process electrical signals received from microphone 124 to generate high-frequency control signals representative of the higher frequency content of sensed acoustic sounds. These control signals are then coupled to stimulator unit 120 through the above-noted conductive link. Responsive to the high-frequency control signals, stimulator unit 120 selectively generates electrical stimuli and applies the electrical stimuli to electrodes 308. In this manner, the basal region 116 of scala tympani 208 (FIG. 3A) is stimulated with electrical stimuli representative of the higher-frequency content of the sensed acoustic sounds. Such electrical stimuli bypass the defective hair cells in basal region 116 of cochlea 140 and directly activate the appropriate nerves 228 causing nerve impulses to be transferred to the brain where they may be perceived as high frequency sounds.

Significantly, the other hair cells in the cochlea, i.e., those in the apical and mid regions of scala tympani 208, as well as within other canals and locations of cochlea 140, retain their normal functionality. That is, these hair cells are able to sense the fluid waves set up by vibrations of oval window 112 corresponding to low-to-mid frequency sounds. Hence, the recipient primarily senses high frequency sounds through the cochlear implant, and primarily senses mid-to-lower frequency sounds through the normal hearing processes of the ear.

Figure 4A:
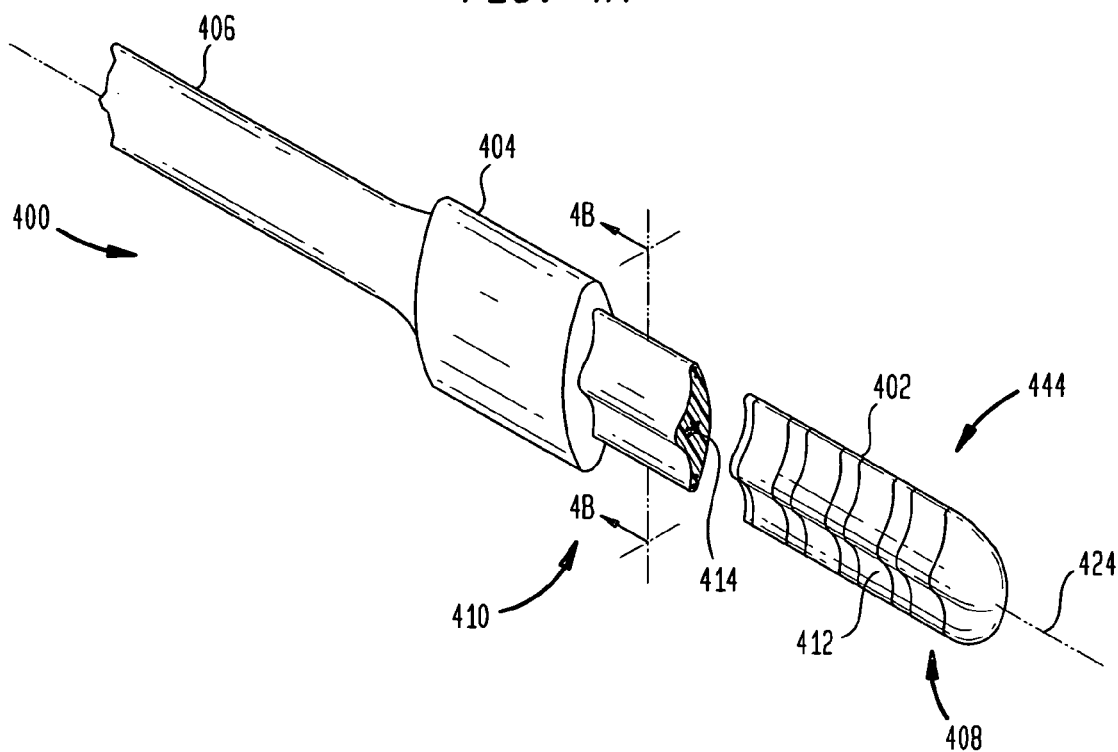
FIG. 4A is a schematic view of an implantable electrode system having an endosteal electrode carrier member in accordance with one embodiment of the present invention.
Figure 4B:
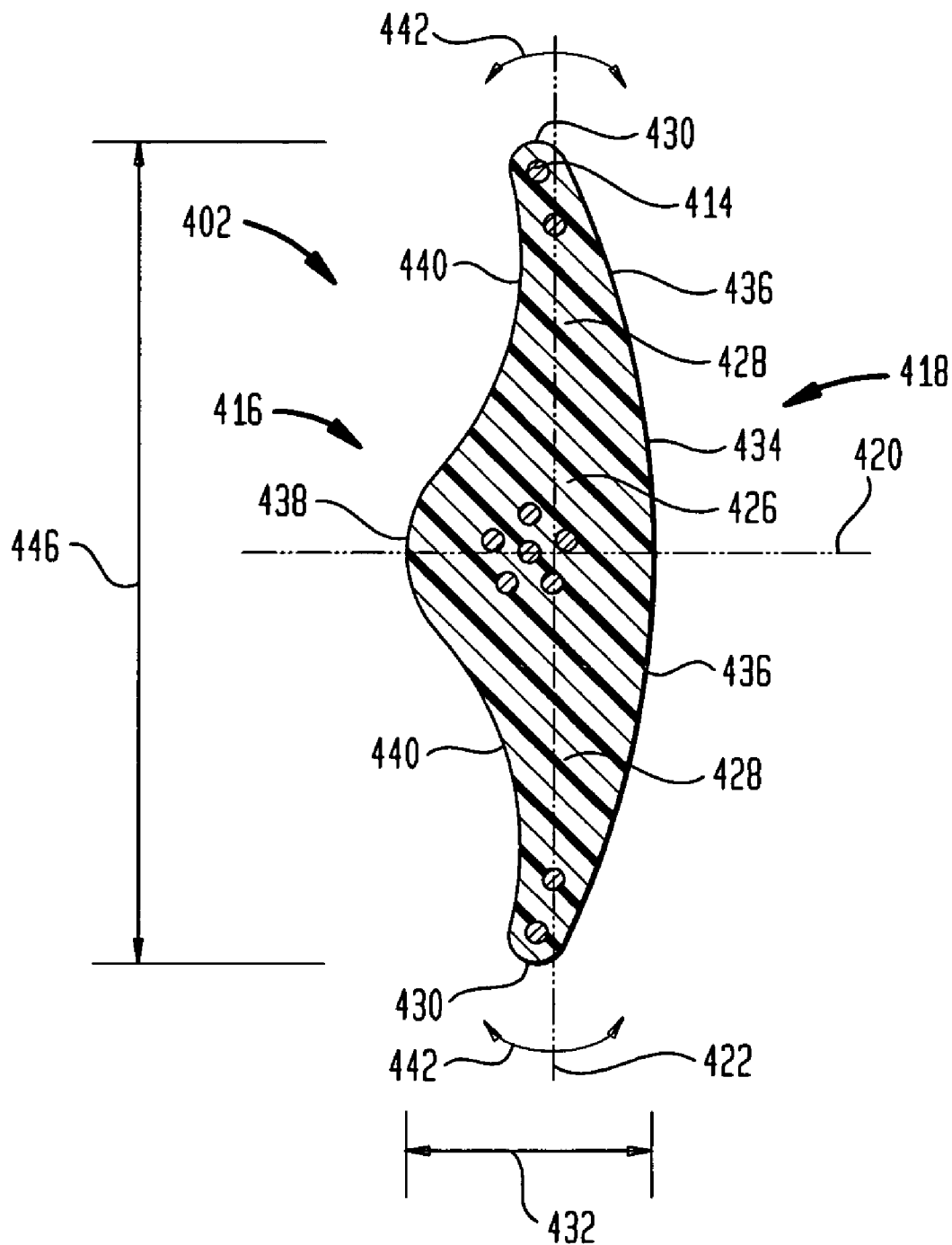
FIG. 4B is a cross-section view of the carrier member illustrated in FIG. 4A.

One embodiment of an electrode assembly of the present invention is described next below with reference to FIGS. 4A and 4B. This embodiment of the electrode assembly, referred to herein as electrode assembly 400, comprises an embodiment of the endosteal electrode carrier member of the present invention advantageously configured for implantation within the cochlea of a recipient. FIG. 4A is a perspective view of electrode assembly 400; FIG. 4B is a cross-sectional view of the endosteal carrier member illustrated in FIG. 4A. In the following description reference will also be made to an alternative embodiment of the electrode assembly, referred to as electrode assembly 500, illustrated in FIGS. 5A-5E. FIGS. 5A, 5B and 5D are side, front and top views, respectively, while FIG. 5C is an enlarged side view of the tip region of electrode assembly 500 and FIG. 5E is a cross sectional view of electrode assembly 500.

Electrode assembly 400 comprises endosteal carrier member 402, stop member 404 and lead 406. Carrier member 402 has a distal end 408 and a proximal end 410 connected to laterally-extending stop member 404 described elsewhere herein. The opposing end of stop member 404 is connected to lead 406 which physically and electrically connects carrier member 404 and electrodes 412 disposed thereon with receiver/stimulator unit 120 (FIG. 1A).

When implanted in a recipient, the surface of carrier member 402 which faces medial side 220 of cochlea 140 is referred to herein as medial surface 416 of carrier member 402. The opposing side of carrier member 402, referred to herein as the lateral surface 418, faces the cochlear bony capsule 216, similar to lateral side 218 of cochlea 140. In the view illustrated in FIG. 4B, medial surface 416 is the left side of carrier member 402 while lateral surface 418 is the right side of carrier member 402. It should be understood that the terms medial surface, medial direction and the like are generally used herein to refer to the surfaces, features and direction toward the center of cochlea 140, while the terms lateral surface, lateral direction and the like are generally used herein to refer to the surfaces, features and direction toward the exterior of cochlea 140.

In addition, a longitudinal plane 420 and a lateral plane 422 (FIG. 4B) are utilized herein to facilitate understanding of the shape and other features of carrier member 402. A longitudinal axis 424 of elongate carrier member 402 lies in longitudinal plane 420.

A plurality of spaced-apart electrodes 412 are mounted on or in carrier member 402. Electrodes 412 may be disposed in a linear or non-linear array on or in carrier member 402, and may be positioned to align with predetermined regions of tonotopically mapped cochlea 140. Such an arrangement allows for individual electrodes 412 to be energized to stimulate selected regions of cochlea 140.

As shown in FIG. 4A, electrodes 412 are, in this embodiment, half-band electrodes disposed on medial surface 416 of carrier member 402. It should be appreciated, however, that any electrodes now or later developed suitable for a particular application may be used in alternative embodiments of the invention. For example, in one alternative embodiment, electrodes 412 are banded electrodes extending substantially around carrier member 402. In another alternative embodiment, electrodes 412 do not laterally extend to or around the edges of carrier member 402. Typically, each electrode 412 is arranged orthogonal to longitudinal axis 424 of carrier member 402, as depicted in FIG. 4A. It should be appreciated, however, that other relative positioning and orientation may be implemented in alternative embodiments. It should further be appreciated that the quantity of electrodes 412 may vary from as few as one or two to as many as twenty-four or more.

In certain embodiments, at least one electrode 412 has a surface that is at least adjacent medial surface 416 of carrier member 402. Preferably, one or more electrodes 412 has a surface that is adjacent medial surface 416 of carrier member 402. In a further embodiment, the surfaces of electrodes 412 are aligned with medial surface 416. In another embodiment, the surfaces of electrodes 412 are raised above medial surface 416 of carrier member 402. In the embodiment illustrated in FIG. 5E, electrodes 512 are recessed into medial surface 516 of carrier member 502.

Electrodes 412 may be manufactured from a biocompatible conductive material such as platinum, although other materials or combinations of materials may be used. Alternatively, electrodes 412 may be coated with a biocompatible covering that does not interfere with transfer of stimulation signals to cochlea 140.

Each electrode 412 is electrically connected to at least one multi- or single-filament wire 414 that is embedded within flexible carrier member 402, stop member 404 and lead 406. In one embodiment, wires 414 are embedded in the volumetric core of carrier member 402. In an alternative embodiment, wires 414 may be located at or near surfaces 416 and/or 418 of carrier member 402. For reasons described elsewhere herein, wires 414 are embedded in different regions of carrier member 402 in the embodiment shown in FIGS. 4A and 4B.

It is through wires 414 that stimulator/receiver unit 120 (FIG. 1A) provides electrical stimuli to selected electrodes 412. In one embodiment, wires 414 are connected to electrodes 412 by welding, although any suitable connecting means now or later developed may be used.

It should be appreciated that the quantity of wires 414 connected to each electrode 412 may vary. For example, in one alternative embodiment, at least two electrically conducting wires 414 are connected to each of one or more electrodes 412. It should also be appreciated that suitable transmission means other than filament wires may be used to communicably couple receiver/stimulator unit 120 and electrodes 412.

In one embodiment, lead 406 may extend from carrier member 402 to stimulator 120 or at least the housing thereof. In one particular embodiment, lead 406 is continuous with no electrical connectors, at least external the housing of stimulator unit 120, required to electrically connect electrode assembly 400 to stimulator 120. One advantage of this arrangement is that there is no requirement for a surgeon implanting electrode assembly 400 to make the necessary electrical connection between wires 414 extending from electrodes 412 and stimulator 120. Stimulator 120 is preferably encased within an implantable housing that is implantable within the implant. The housing for the stimulator is preferably implantable within a recess in the bone behind the ear posterior to the mastoid.

In one embodiment, lead 406 may extend from carrier member 402 to the stimulator unit or at least the housing thereof. In an embodiment of the present invention, lead 406 is continuous with no electrical connectors, at least external the housing of the stimulator, required to connect the wires extending from the electrodes to the stimulator. One advantage of this arrangement is that there is no requirement for the surgeon implanting the device to make the necessary electrical connection between the wires extending from the electrodes and the stimulator. The stimulator is preferably positioned within a housing that is implantable within the implant. The housing for the stimulator is preferably implantable within a recess in the bone behind the ear posterior to the mastoid.

As noted, elongate electrode carrier member 402 is configured to be implanted in pocket 302 external to cochlear canals 202 to position electrodes 412 sufficiently proximate to organ of Corti 210 to effectively deliver stimulation signals to auditory nerve fibers 212 of cochlea 140.

Carrier member 402 comprises an elongate central region 426 and integral elongate side regions 428. In the embodiment shown in FIGS. 4A and 4B, side regions 428 lie in lateral plane 422; that is, they laterally extend from opposing sides of central region 426. In addition, side regions 428 are substantially uniform in dimensions and/or orientation. As such, this embodiment of carrier member 402 is substantially symmetrical about longitudinal plane 20.

Central region 426 is bulbous while side regions 428 are tapered from central region 426 to their respective edge surfaces 430. As such, central region 426 has a cross-sectional volume and a thickness 432 that is greater than that of side regions 428. In addition, the surface tangent of medial surface 416, lateral surface 418 and edge surfaces 430 changes gradually to form a smooth, contiguous surface with no sharp or locally discrete edges or corners. Each of these surfaces 418, 416 and 430 are described in detail next below.

The surface 434 of central region 426 forming a portion of lateral surface 418 has a curved shape with a substantially consistent radius of curvature. Similarly, the shape of the surface 436 of side regions 428 which form a portion of lateral surface 418 each are similarly curved and also have a consistent radius of curvature. As shown in FIG. 4B, the radius of the central and side region surfaces 434, 436 is substantially the same, resulting in a carrier member lateral surface 418 which has a substantially consistent radius. In one embodiment, the curvature of lateral surface 418 is approximately the same as the curvature of the endosteum along the basal turn of cochlea 140. This similarity in curvature urges carrier member 402 to remain in its implanted position.

With regard to medial surface 416, the surface is contoured to provide certain of the noted features of carrier member 402. For example, to achieve a desired taper of side regions 428 while providing the above-noted lateral surface 418 while also avoiding discrete changes in the surface slope of carrier member 402, the surface 440 of side regions 428 which form a portion of medial surface 416 are incurvatured as shown best in FIG. 4B. In certain embodiments, the incurvature is greater, forming a concave shape, while in other embodiments, the incurvature is minimal. In still other embodiments, there is no incurvature; surfaces 440 are substantially planar.

The surface 438 of central region 426 which forms a portion of medial surface 416 has a convex shape in the embodiment shown in FIGS. 4A and 4B. As noted, electrodes 412 are disposed in or on at least medial surface 416 of carrier member 402. Thus, when implanted in crevice 302, electrodes 412 extend toward the organ of Corti 210 to facilitate electrical stimulation.

It should be appreciated that the radius of curvature of concave surface 438 and incurvatured surfaces 440 may be different in alternative embodiments depending, for example, on the relative thickness of central region 426 and side regions 428, the desired rate of change of surface slope across medial surface 416, and the desired proximity of electrodes 412 disposed on the surface of central region 428. For example, in the embodiment illustrated in FIG. 5B, surfaces 536 of side regions 528 have a relatively smaller incurvature than their counterparts in the embodiment illustrated in FIGS. 4A and 4B.

Turning to edge surfaces 430, tapered side regions 428 have an edge surface 430 which provides a transition between opposing medial and lateral surfaces 416, 418. As shown in FIGS. 4A and 4B, edge surfaces 430 have no sharp edges. Rather, edge surfaces 430 have a minimum radius of curvature which is greater than zero to provide a smooth, curved edge on carrier member 402. This reduces the likelihood that the edges surfaces 430 of carrier member 402 may damage cochlea 140 or its surrounding anatomy during or after implantation.

It should also be appreciated that this enables carrier member 402 to have a width that is substantially the same as the width of crevice 302. In such an application, once implanted, tapered side regions 428 laterally extend from central region 426 into the corners of crevice 302 thereby urging carrier member 402 to remain in its implanted orientation and position without causing the development of lesions. Embodiments in which side regions 428 are flexible, described elsewhere herein, further enhance this advantage.

As noted, embodiments of carrier member 402 have a minimized volume to facilitate implantation into crevice 302. This reduced cross-sectional volume may cause carrier member 402 to bend in unintentional directions during implantation. To prevent this from occurring, embodiments of carrier member 402 have longitudinally-extending structural support in central region 426. In the embodiment shown in FIGS. 4A and 4B, such support is provided by the distribution of embedded wires 414. In alternative embodiments, such structural support may be provided by other materials embedded in carrier member 402, by varying the density or materials used to form carrier member 402, etc. Such configurations increase the "pushability" and "trackability" of carrier member 402 during the insertion procedure into crevice 302. It should be appreciated, however, that such rigidity should not prevent carrier member 402 from being able to coil or turn in longitudinal plane 420 so that it may follow the contour of cochlea 140 during implantation. In other words, such structural support serves to increase the longitudinal rigidity and, perhaps, limit curving in lateral plane 422 while permitting curving in longitudinal plane 420.

As noted, side regions 428 are resiliently flexible, allowing them to flex along directions 442 out of lateral plane 422. In such embodiments, side regions 428 serve to guide the direction of travel of carrier member 402, flexing out of lateral plane 422 as necessary to avoid damaging anatomical structures. This construction facilitates implantation of carrier member 402. Central region 426 has sufficient longitudinal strength to maintain its form and direction while being pushed into surgical pocket 302; carrier member 402 coils in longitudinal plane 420 while side regions 428 serve to guide the direction of travel, flexing out of lateral plane 422 as necessary to avoid damaging anatomical structures. Accordingly, such an embodiment of carrier member 402 may be more resiliently flexible in longitudinal plane 420 and relatively less resiliently flexible in lateral plane 422. Carrier member 402 may be adapted to follow the curvature of the endosteum along the basal turn of cochlea 140. In some embodiments, the shape and curvature of side regions 428 may provide increased resistance to movement in lateral plane 422 while permitting flexibility in longitudinal plane 420.

In one embodiment, the thickness 432 of carrier member 402 between medial surface 416 and lateral surface 418 is substantially constant for at least a majority of its length from distal end 408 to proximal end 410. In certain embodiments, a longitudinally-tapered tip region 444 is formed adjacent distal end 408. In one embodiment, thickness 432 of central region 426 gradually tapers toward distal end 408. Tip region 444 facilitates the insertion of carrier member 402 into a recipient's cochlea. In one embodiment, tip member region 444 comprises a taper which slopes from a lateral surface 418 rearward and inward toward the medial surface 416. Such a tapered tip region 444 aids the coiling of carrier member 400 and further helps prevent damage to the delicate structures of the cochlea.

An alternative embodiment of a tip region of the present invention is illustrated in FIGS. 5A and 5C. In this embodiment, tip region 544 as a rounded surface 548 extending from medial surface 516 to front surface 546, and a rounded surface 550 extending from lateral surface 518 to front surface 546. Thus, in this embodiment, both sides of carrier member 502 are tapered, with each having a different radius.

Another alternative embodiment of a tip region is illustrated in FIG. 6. Here, tip region 644 has a bottle-nose configuration. That is, at tip region 644 medial surface 616 is curved 650 toward lateral surface 618. An extension 652 extends beyond curvature 650 to form a plateau 654. The leading edge of extension 652 is curved or rounded to provide a blunt leading surface on a carrier member implanting tip region 644. The radius of curvature of curved surface 650 is preferably gradual to avoid abrasions.

Referring back to FIG. 4A, stop member 404 serves as both a region for grasping electrode assembly 400 and also acts to prevent insertion of carrier member 402 within crevice 302 beyond a predetermined maximum depth. In one embodiment, the predetermined maximum depth is approximately 8 to 10 mm.

In the embodiment shown in FIG. 4A, stop member 404 has a diameter slightly greater than that of carrier member 402. As one of ordinary skill in the art should appreciate, the configuration, orientation and dimensions of stop member 404 can vary depending on the intended application of electrode assembly 400. In one embodiment, stop member 404 extends substantially at right angles to the longitudinal axis 424 of carrier member 402. In another embodiment of the present invention, stop member 404 has a length of between about 1.5 and about 2.0 mm. One alternative embodiment of the stop member of the present invention is illustrated in FIGS. 5A and 5B. In this embodiment, stop member 504 has a length which is greater than the length of stop member 404, and the transition between stop member 504 and carrier member 502 is tapered. In another embodiment, the stop member is a tab shaped extension integral with carrier member 402.

In one embodiment, endosteal carrier member 402 has a length of approximately 10 mm, a width 446 of about 1.2 mm, and a thickness 432 of approximately 0.2 mm. These dimensions are exemplary only; the dimensions may vary as needed for a particular application. In particular, the length of endosteal carrier member 402 may vary from as short as approximately 4 mm to as long as approximately 30 mm in certain embodiments. In an alternative embodiment, carrier member 402 has a length of about 7 to about 10 mm, a width 446 of about 0.6 mm and a thickness 432 of about 0.2 mm or less and, preferably, about 0.1 mm. In another embodiment, carrier member 402 may have a width 446 of about 200 μm to about 600 μm, and preferably about 300 μm, and a thickness 432 of between about 60 μm and about 150 μm and, preferably, about 120 μm.

In a further embodiment, thickness 432 of carrier member 402 between its medial surface 416 and its lateral surface 418 may be substantially constant for at least a majority of its length from proximal end 410 the distal end 408. In another embodiment, thickness 432 of carrier member 402 may change, such as decrease, along its length as well.

As one of ordinary skill in the art would understand, the implantable electrode assembly of the present invention may be manufactured using any technique known now or developed in the future. In one embodiment, carrier member 402 may be formed from a resiliently flexible biocompatible elastomeric material such as silicone. In another embodiment, carrier member 402 may be formed from a biocompatible polyurethane or similar material.

Further features of the present invention may be discerned from the following disclosures: Pau H W, Cochlear implants:

concepts and ideas about an endosteal electrode, Invited lecture, VII Internat. Conf. on Cochlear Implants, Warsaw, Poland, 2003; Pau H W, Behrend D, Just T, Lehnhardt, Is an endosteal electrode for cochlear implantation basically feasible?, 24th Pulitzer Society Meeting, Amsterdam, 2003; Pau H W, Lehnhardt E, Positioning of the endosteal electrode laterally to the spiral ligament, Investigations in human temporal bones, 4th Int. Symp. on Electronic Implants in Otology+Conventional Hearing Aids, Toulouse, 2003; Pau H W, Just T, Hessel H, Lehnhardt E, Behrend D, An endosteal electrode for cochlear implantation in cases of residual hearing?, Laryngoscope, 2004; Souffrant R, Behrend D, Pau H W, Lehnhardt E, Schmitz K P, Innenohrschonende Cochlear-Implantat-Elektrode, Eine anatomisch-histologische Studie am menschlichen Felsenbeinpräparat, Biomed. Technik, 2003, 48: 327-330; and Pau H W, Endosteal cochlear electrode, Invited lecture, Cochlear Company, Sydney, Australia, October 2003, the entire contents and disclosures of which are hereby incorporated by reference herein.

As noted, aspects of the present invention is directed to a cochlear electrode carrier member that does not interfere with the normal functioning of inner ear 107. One application for the present invention is for use with a hybrid cochlear stimulation system. Another application for the present invention is for use to supplement the normal hearing processes as described above with reference to FIG. 3B. Yet another application is for use of the electrode array, inserted under the spiral ligament membrane at the lateral wall of the cochlea, is to selectively energize the electrodes of the array in order to treat tinnitus.

Where the device is being used to mask or treat the symptoms of tinnitus, the external controller may comprise a processor adapted to output one or more stimulation regimes to the stimulator. In an embodiment of the present invention, the stimulation regime may comprise a random continuous subthreshold stimulation regime. In this regime, the stimulation signals output to the electrodes of the carrier member are at a level below the threshold of hearing of the sufferer. In another embodiment, the stimulation regime may comprise a random continuous supra-threshold stimulation, such as white noise. In a still further embodiment, the stimulation regime may comprise a random discontinuous supra-threshold stimulation regime. According to an embodiment of the present invention, irregular stimulation may be sufficient to reduce the impact of the tinnitus condition. Irregular stimulation also has the advantage of being relatively power-efficient and hence would result in longer battery life for the device. In yet a further embodiment, the stimulation regime may comprise a treatment-on-demand regime. Such a regime is postulated by the present inventors as being advantageous for those persons who only suffer irregular episodes of tinnitus. In this embodiment, the external controller may further comprise an activation means. The activation means may comprise a switch means on the external controller. In this case, the sufferer or a third person could activate the processor when required.

In one use of the system, the stimulation regimes of stimulator 102 are designed to mask or treat the symptoms of tinnitus. In one embodiment, the stimulation regime may comprise a random continuous sub-threshold stimulation regime. In this regime, the stimulation signals output to the electrodes of a carrier member are at level below the threshold of hearing of the implantee.

In yet a further embodiment, the stimulation regime may comprise a treatment-on-demand regime. In this embodiment, controller 104 may further comprise an activation means 112. Activation means 112 comprises a switch on controller 104. In this case, the implantee or a third person could activate the processor when required.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All documents, patents, journal articles and other materials cited in the present application are hereby incorporated by reference. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom. In addition, the described embodiments, whether described with reference to the same or a different aspect of the invention, may be combined in any way desirable that is not conflicting or otherwise not possible. Thus, any particular implementation or embodiment may be combined or implemented with any other non-conflicting embodiment.

What is claimed is:

1. An elongate carrier member comprising:
   a longitudinally-extending central region;
   two side regions laterally extending from opposing sides of the central region such that the carrier member is substantially symmetrical about a longitudinal plane;
   a lateral surface defined by the central and side regions together forming a convex circumferential surface defined by a single radius;
   a medial surface defined by a convex surface of the central region and a concave surface for each of the side regions;
   a plurality of longitudinally-spaced electrodes disposed on or in the convex surface of the central region of the medial surface; and
   a support structure comprising a plurality of longitudinally extending wires each connected to one or more of the electrodes, wherein a subset of the plurality of wires is disposed in the central region and at least one of the plurality of wires is disposed in one of the side regions.

2. The carrier member of claim 1, wherein the carrier member is resiliently flexible in the longitudinal plane.

3. The carrier member of claim 2, wherein the carrier member is less resiliently flexible in a lateral plane than the longitudinal plane.

4. The carrier member of claim 2, wherein the side regions are resiliently flexible in a lateral plane.

5. The carrier member of claim 4, wherein the side regions are configured to flex when the carrier member is implanted in a crevice between the spiral ligament and the endosteum of the lateral wall of the cochlea.

6. The carrier member of claim 1, wherein the side regions each have a smooth end edge that connects the lateral surface to the medial surface.

7. The carrier member of claim 1, wherein the curvature of the lateral surface approximates the curvature of the endosteum along the basal turn of the cochlea.

8. The carrier member of claim 1, further comprising a stop member at a proximal end of the carrier member.

9. The carrier member of claim 1, further comprising a tip member at a distal end of the carrier member.

10. The carrier member of claim 9, wherein the tip member comprises:

a first rounded surface extending from the medial surface to a front surface and having a first taper defined by a first radius; and a second rounded surface extending from the lateral surface to the front surface and having a second taper defined by a second radius;

wherein the first radius and the second radius are different.

11. The carrier member of claim 9, wherein, at the tip member, the medial surface curves towards the lateral surface; and wherein the tip member comprises an extension that longitudinally extends beyond said curving medial surface to form a plateau and which has a blunt leading surface.

12. The carrier member of claim 1, wherein at least one of the plurality of wires is disposed in a first one of the two side regions and at least one of the plurality of wires is disposed in a second one of the two side regions.

13. A hearing prostheses comprising:

an implantable stimulator; and an electrode array connected to the stimulator, the array comprising:

an elongate carrier member having a contiguous smooth shape defined by a lateral convex surface having a substantially consistent radius of curvature and which curves at each end to meet a medial surface having two symmetrical concavities about a longitudinal plane that define a central region having a convex surface and two opposing side regions, wherein the thickest part of the carrier member is near the central region, wherein the carrier member comprises a plurality of electrodes disposed on or in the convex surface of the central region of the medial surface; and wherein the carrier member further comprises a support structure comprising a plurality of longitudinally extending wires each connected to one or more of the electrodes, wherein a subset of the plurality of wires is disposed in the central region and at least one of the plurality of wires is disposed in one of the side regions.

14. The prostheses of claim 13, wherein the carrier member is resiliently flexible in the longitudinal plane.

15. The prostheses member of claim 14, wherein the carrier member is less resiliently flexible in a lateral plane than the longitudinal plane.

16. The prostheses member of claim 14, wherein the side regions are resiliently flexible in a lateral plane.

17. The prostheses of claim 16, wherein the side regions are configured to flex when the carrier member is implanted in a crevice between the spiral ligament and the endosteum of the lateral wall of the cochlea.

18. The prostheses of claim 13, wherein the side regions each have a smooth end edge that connects the lateral surface to the medial surface.

19. The prostheses of claim 13, wherein the curvature of the lateral surface approximates the curvature of the endosteum along the basal turn of the cochlea.

20. The prostheses of claim 13, further comprising a tip member at a distal end of the carrier member.

21. The prostheses of claim 20, wherein the tip member comprises:

a first rounded surface extending from the medial surface to a front surface and having a first taper defined by a first radius; and a second rounded surface extending from the lateral surface to the front surface and having a second taper defined by a second radius;

wherein the first radius and the second radius are different.

22. The prostheses of claim 20, wherein, at the tip member, the medial surface curves towards the lateral surface; and wherein the tip member comprises an extension that longitudinally extends beyond said curving medial surface to form a plateau and which has a blunt leading surface.

23. The prosthesis of claim 13, wherein at least one of the plurality of wires is disposed in a first one of the two side regions and at least one of the plurality of wires is disposed in a second one of the two side regions.

\* \* \* \* \*